United States Patent [19]

Rosenberger

[11] 4,417,071
[45] Nov. 22, 1983

[54] PHENOLS USEFUL AS STABILIZERS

[75] Inventor: Siegfried Rosenberger, Riehen, Switzerland

[73] Assignee: Ciba-Geigy Corporation, Ardsley, N.Y.

[21] Appl. No.: 357,248

[22] Filed: Mar. 11, 1982

Related U.S. Application Data

[63] Continuation of Ser. No. 127,015, Mar. 4, 1980, abandoned.

[51] Int. Cl.³ ............................................. C07C 69/88
[52] U.S. Cl. ......................................... 560/67; 560/57; 560/65; 560/75; 260/45.85 B
[58] Field of Search ............................... 560/67, 65, 75

[56] References Cited
FOREIGN PATENT DOCUMENTS
1948570  4/1970  Fed. Rep. of Germany ........ 560/67

*Primary Examiner*—Paul J. Killos
*Attorney, Agent, or Firm*—Luther A. R. Hall

[57] ABSTRACT

A process for the manufacture of phenols of the formula I

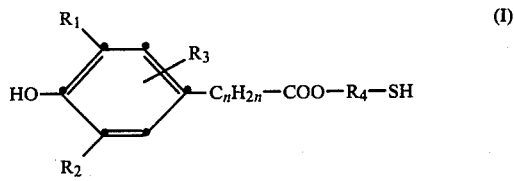

wherein $R_1$ is alkyl of 1 to 18 carbon atoms, cycloalkyl, phenyl, aralkyl or chlorine, $R_2$ is hydrogen or has the same meaning as $R_1$, $R_3$ is hydrogen or alkyl of 1 to 12 carbon atoms, $R_4$ is alkylene of 2 to 18 carbon atoms which is unsubstituted or substituted by aryl or hydroxyl, and n is an integer from 0 to 4, which process comprises transesterifying a compound of the formula II

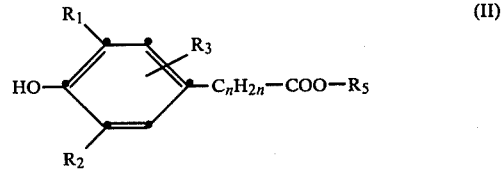

wherein $R_1$, $R_2$ and $R_3$ are as defined for formula (I) and $R_5$ is alkyl of 1 to 4 carbon atoms with a mercapto alcohol of the formula

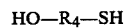

wherein $R_4$ is as defined for formula (I), in the presence of a catalyst of the formula $(R_6O)_4M$, wherein $R_6$ represents alkyl radicals of 1 to 18 carbon atoms which can be the same or different, aryl or alkaryl, and M is an element selected from the group consisting of Ti, Ge, Zr, Sn or V.

8 Claims, No Drawings

PHENOLS USEFUL AS STABILIZERS

This is a continuation of application Ser. No. 127,015, filed on Mar. 4, 1980, now abandoned.

The present invention relates to organic material stabilised with phenols and to a process for the manufacture of these phenol stabilisers.

The manufacture of 2-mercaptoethyl 3-(3,5-di-tert-butyl-4-hydroxyphenyl)propionates is described in French patent specification No. 2 018 870. According to this patent, these compounds are useful intermediates for the manufacture of stabilisers for polymers. In a two-step process, the methyl ester of 3,5-dialkyl-4-hydroxyphenylcarboxylic acid is first saponified and then esterified with the mercapto alcohol. The esterification step is carried out in the presence of an acid catalyst.

In order to eliminate the drawbacks of a two-step process, attempts have been made to find methods of direct esterification. It has become evident that direct esterification with acid catalysts leads to only very poor results. Experiments using basic catalysts, such as LiNH$_2$, have also proved unsatisfactory. Previous experience has shown that the desired final product is obtained either in too low a yield or in such impure form that required purification is necessary.

An uncomplicated process for the manufacture of the compounds of the formula I has now been found, which process, surprisingly, can be carried out in a single step.

Accordingly, the present invention provides a process for the manufacture of phenols of the formula I

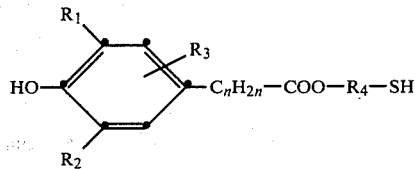

wherein R$_1$ is alkyl of 1 to 18 carbon atoms, cycloalkyl, phenyl, aralkyl or chlorine, R$_2$ is hydrogen or has the same meaning as R$_1$, R$_3$ is hydrogen or alkyl of 1 to 12 carbon atoms, R$_4$ is alkylene of 2 to 18 carbon atoms which is unsubstituted or substituted by aryl or hydroxyl, and n is an integer from 0 to 4, which process comprises transesterifying a compound of the formula II

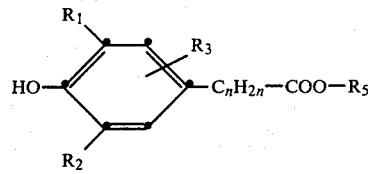

wherein R$_1$, R$_2$ and R$_3$ are as defined for formula (I) and R$_5$ is alkyl of 1 to 4 carbon atoms, with a mercapto alcohol of the formula

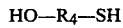

HO—R$_4$—SH wherein R$_4$ is as defined for formula (I), in the presence of a catalyst of the formula (R$_6$O)$_4$M, wherein R$_6$ represents alkyl radicals of 1 to 18 carbon atoms which can be the same or different, aryl or alkaryl, and M is an element selected from the group consisting of Ti, Ge, Zr, Sn or V.

The reactants can be employed in the molar ratio of 1:1 to 1:3, based on the ester of the formula I to the mercapto alcohol. The preferred molar ratio is 1:1 to 1:2. The catalyst can be employed preferably in an amount from 0.01 to 2.0 mol%, most preferably from 0.1 to 1.0 mol%. The reaction can be carried out in the temperature range from 50° to 200° C., preferably from 120° to 180° C., over the course of 5 to 25 hours.

The process can be carried out both in the presence and in the absence of a solvent. If a solvent is employed, then it may suitably be an unsubstituted or a chlorinated aliphatic or aromatic hydrocarbon, or also an ether. Examples of such solvents are ligroin, benzene, toluene, chloroform, chlorobenzene, dichloroethane, dioxane or diethyl ether. It is preferred to carry out the reaction in the absence of a solvent.

R$_1$ and R$_2$ as C$_1$–C$_{18}$alkyl are e.g. methyl, isopropyl, n-butyl, sec-butyl, tert-butyl, tert-amyl, 2-ethylhexyl, n-octyl, tert-octyl, n-dodecyl, 1,1,7,7-tetramethyloctyl, n-octyldecyl, α-branched alkyl radicals containing 3 to 8 carbon atoms are preferred, e.g. isopropyl, tert-butyl, tert-armyl and tert-octyl. Tert-butyl, but also methyl, is especially preferred.

R$_1$ and R$_2$ as cycloalkyl are e.g. cyclopropyl, cyclopentyl, cyclohexyl, cycloheptyl, cyclooctyl or cyclododecyl. Cyclopentyl and cyclohexyl are preferred.

R$_1$ and R$_2$ as aralkyl can be benzyl, or preferably, α-phenylethyl and 2-phenylisopropyl.

It is preferred that R$_1$ and R$_2$ are tert-butyl.

R$_3$ as C$_1$–C$_{12}$alkyl can be methyl, ethyl, isopropyl, n-butyl, tert-butyl, 2-ethylhexyl, tert-octyl, n-decyl, 1,1-dimethyldecyl or, preferably, methyl. It is preferred, however, that R$_3$ is hydrogen.

R$_4$ as C$_2$–C$_{18}$alkylene can be e.g. 1,2-ethylene, 1,2-propylene, 1,3-propylene, 1,2-butylene, 1,4-butylene, 1,6-hexymethylene, 2,9-decylene or 1,6-hexadecamethylene. Preferably, R$_4$ is C$_2$–C$_4$alkylene, e.g. 1,2-ethylene, 1,3-propylene and 1,4-butylene. The most preferred identity for R$_4$ is 1,2-ethylene.

n as an integer from 0 to 4 has preferably a value from 1 to 4. The most preferred value of n is 2 or 4.

C$_1$–C$_{18}$Alkyl radicals represented by R$_6$ can be the same as those specified for R$_1$. Preferably R$_6$ is C$_1$–C$_4$alkyl and, most preferably, is n-propyl or n-butyl.

R$_6$ as aryl can be e.g. phenyl, α-naphthyl or β-naphthyl, with phenyl being preferred.

R$_6$ as alkaryl can be e.g. tolyl, xylyl, 2,6-diethylphenyl or 4-tert-butylphenyl.

M is preferably Ti, Ge, Sn, Zr or V, most preferably Ti.

Examples of compounds of the formula I are:
2-mercaptoethyl 2,3-dimethyl-5-tert-butyl-4-hydroxyphenyl (2,2-dimethyl)propionate,
2-mercapto-2-phenyl 2,3-dimethyl-5-tert-butyl-4-hydroxyphenylpropionate,
2-mercaptoethyl 3-methyl-5-tert-butyl-4-hydroxyphenylpropionate,
2-mercaptopropyl 3,5-di-tert-octyl-4-hydroxyphenylpropionate,
2-mercaptobutyl 3,5-di-tert-butyl-4-hydroxyphenylvalerate,
2-mercaptoethyl 3,5-di-tert-butyl-4-hydroxyphenylpropionate,
2-mercaptoethyl 3,5-di-tert-butyl-4-hydroxyphenylbenzoate.

The compounds of the formula I are known from French patent specification No. 2 018 870 as intermediates for the manufacture of stabilisers for polymers.

It has now been found that the compounds are themselves effective stabilisers. Accordingly, the invention also relates to stabilised organic material containing, as stabiliser, a compound of the formula I.

The compounds of the formula I are effective antioxidants for organic material. They are suitable for stabilising a large number of organic polymers and also natural and synthetic elastomers, e.g.:

1. Polymers that are derived from mono- and diolefins, such as uncrosslinked or crosslinked polyethylene, polypropylene, polyisobutylene, polymethylbutene-1, polymethylpentene-1, polyisoprene, polybutadiene.
2. Mixtures of the homopolymers listed in (1) above, e.g. mixtures of polypropylene and polyethylene, polypropylene and polybutene-1, polypropylene and polyisobutylene.
3. Copolymers of the monomers based on the homopolymers listed in (1) above, such as copolymers of ethylene and propylene, copolymers of ethylene and butene-1, and terpolymers of ethylene and propylene with a diene, e.g. hexadiene, dicyclopentadiene or ethylidene.
4. Acrylonitrile copolymers, e.g. the copolymer of butadiene-acrylonitrile-methylmethacrylate, and ABS.
5. Polystyrene and its copolymers, such as styrene copolymers modified with SAN, IPS, ASA and EP.
6. Halogenated vinyl polymers.
7. Polyurethanes and polyureas.
8. Polycarbonates.
9. Polyamides.
10. Polyesters.
11. Elastomers, such as polybutadiene, SBR, polyisoprene, polychloroprene and nitrile rubber.
12. Thermoplastic elastomers, such as SBS, SIS and S-EP-S.

The compounds of the present invention are suitable in particular for stabilising acrylonitrile copolymers, such as the copolymer of butadiene-acrylonitrile-methylmethacrylate, and ABS.

The compounds of the invention are especially effective stabilisers when they are grafted onto the polymer in the presence of radical former. Radical formers and polymers suitable for this purpose are described in German Offenlegungsschrift No. 2 509 654 and GB Pat. No. 1,503,501 respectively.

The use of the phenols of the formula I in this manner constitutes a further object of the invention.

Further, the compounds of the formula I are effective stabilisers for synthetic and mineral lubricating oils and circulating oils.

The stabilisers can be combined, if desired, with other additives, such as other antioxidants, lubricants such as calcium stearate, pigments, dyes, UV-absorbers, sterically hindered amines as light stabilisers, metal deactivators, talc, and other fillers.

As a rule, the stabilisers of the invention are employed in amounts from 0.01 to 5% by weight, based on the stabilised material. The amount can differ, depending on the substrate and utility. The stabilisers are preferably employed in amounts from 0.05 to 2%, most preferably from 0.1 to 1%, by weight.

The compounds of the formula I can be incorporated with ease into the organic polymer by the conventional methods and in any phase during the production of moulded articles.

As described above, the compounds of the formula I are excellent stabilisers for polymers and lubricating oils. They are obtained by the single-step process in high yield and great purity.

The invention is illustrated by the following Examples.

EXAMPLE 1

2-Mercaptoethyl 3,5-di-tert-butyl-4-hydroxyphenylpropionate 438 of methyl 3,5-di-tert-butyl-4-hydroxyphenylpropionate are fused in a reaction vessel at 155° C. and then 1.5 ml of tetra-n-butyl-o-titanate are added to the melt. The apparatus, which is equipped with a reflux cooler warmed to 70° C. and descending cooler and cooling trap, is evacuated to about 200 mm Hg. With stirring, 140 g of 2-mercaptoethanol are then added dropwise in the course of 4 hours and the mixture is subsequently stirred for 5 hours. A further 36 g of 2-mercaptoethanol are added in the course of 1 hour and the reaction mixture is stirred for 7 hours at 155° C. and 300 mm Hg, in the course of which about 55 ml of methanol are distilled off. Virtually no more educt is visible in a gas chromatogram. To the contents of the flask are added 700 ml of toluene and 30 g of fuller's earth ("Tonsil Ac"; Süd-Chemie, Munich) at about 100° C. The mixture is boiled briefly, filtered, and the toluene is removed in vacuo from the filtrate, affording the chromatographically pure product which, after inoculation, solidifies to a slightly yellowish crystalline substance, with a melting point of 50° C. Yield: 485 g (95% of theory, based on the methyl ester employed).

EXAMPLE 2

2-Mercaptoethyl 3-methyl-5-tert-butyl-4-hydroxyphenylpropionate

The procedure of Example 1 is repeated, except that methyl 3-methyl-5-tert-butyl-4-hydroxyphenylpropionate is used instead of 2-mercaptoethyl 3,5-di-tert-butyl-4-hydroxyphenylpropionate. The resultant 2-mercaptoethyl-3-methyl-5-tert-butyl-4-hydroxyphenylpropionate is an almost colourless, viscous oil. It is obtained in the same high yield and purity as the product of Example 1.

What is claimed is:

1. A process for the manufacture of a phenol of the formula I

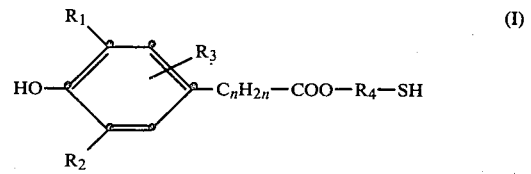

wherein $R_1$ is alkyl of 1 to 18 carbon atoms, cycloalkyl, phenyl, aralkyl or chlorine, $R_2$ is hydrogen or has the same meaning as $R_1$, $R_3$ is hydrogen or alkyl of 1 to 12 carbon atoms, $R_4$ is alkylene of 2 to 18 carbon atoms which is unsubstituted or substituted by aryl or hydroxyl, and n is an integer from 0 to 4, which process comprises transesterifying a compound of the formula II

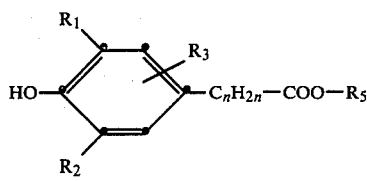

wherein $R_1$, $R_2$ and $R_3$ are as defined for formula (I) and $R_5$ is alkyl of 1 to 4 carbon atoms, with a mercapto alcohol of the formula $$HO-R_4-SH$$

wherein $R_4$ is as defined for formula (I), in the presence of a catalyst of the formula $(R_6O)_4M$, wherein $R_6$ represents alkyl radicals of 1 to 18 carbon atoms which can be the same or different, aryl or alkaryl, and M is an element selected from the group consisting of Ti, Ge, Zr, Sn or V.

2. A process according to claim 1 for the manufacture of a phenol of the formula I

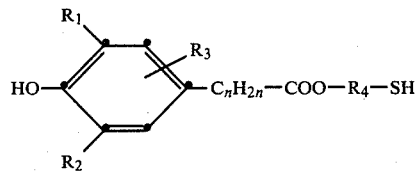

wherein $R_1$ is alkyl of 1 to 18 carbon atoms, cycloalkyl or aralkyl $R_2$ is hydrogen or has the same meaning as $R_1$, $R_3$ is hydrogen or alkyl of 1 to 12 carbon atoms, $R_4$ is alkylene of 2 to 18 carbon atoms which is unsubstituted or substituted by aryl, and n is an integer from 0 to 4, which process comprises transesterifying a compound of the formula II

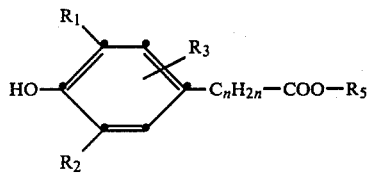

wherein $R_1$, $R_2$ and $R_3$ are as defined for formula (I) and $R_5$ is alkyl of 1 to 4 carbon atoms, with a mercapto alcohol of the formula $$HO-R_4-SH$$

wherein $R_4$ is as defined for formula (I), in the presence of a catalyst of the formula $(R_6O)_4M$, wherein $R_6$ represents alkyl radicals of 1 to 18 carbon atoms which can be the same or different, and M is Ti.

3. A process according to claim 1, wherein the catalyst is tetraalkyl-ortho-titanate, in which the alkyl moieties are the same or different and contain 1 to 4 carbon atoms.

4. A process according to claim 1, wherein the transesterification is carried out in the temperature range from 50° to 200° C.

5. A process according to claim 1, wherein the transesterification is carried out in the temperature range from 120° to 180° C.

6. A process for the manufacture of a phenol of the formula I according to claim 1, wherein $R_1$ and $R_2$ are $C_1$-$C_8$alkyl, cyclopentyl or cyclohexyl, $R_3$ is hydrogen, $R_4$ is $C_2$-$C_4$alkylene or phenylethylene and n is an integer from 1 to 4.

7. A process for the manufacture of a phenol of the formula I according to claim 1, wherein $R_1$ and $R_2$ are α-branched alkyl of 3 to 8 carbon atoms, $R_3$ is hydrogen, $R_4$ is ethylene, 1,3-propylene or 1,4-butylene, and n is 2 or 4.

8. A process for the manufacture of a phenol of formula I according to claim 1 wherein $R_1$ and $R_2$ are each tert-butyl, $R_3$ is hydrogen, $R_4$ is ethylene, and n is 2.

* * * * *